(12) United States Patent
Remiarz et al.

(10) Patent No.: US 10,578,539 B2
(45) Date of Patent: Mar. 3, 2020

(54) REDUCING FALSE COUNTS IN CONDENSATION PARTICLE COUNTERS

(71) Applicant: TSI Incorporated, Shoreview, MN (US)

(72) Inventors: Richard Remiarz, Vadnais Heights, MN (US); Kenneth Farmer, Lake Elmo, MN (US)

(73) Assignee: TSI Incorporated, Shoreview, MN (US)

( * ) Notice: Subject to any disclaimer, the term of this patent is extended or adjusted under 35 U.S.C. 154(b) by 0 days.

(21) Appl. No.: 16/089,777

(22) PCT Filed: Mar. 31, 2017

(86) PCT No.: PCT/US2017/025403
§ 371 (c)(1),
(2) Date: Sep. 28, 2018

(87) PCT Pub. No.: WO2017/173285
PCT Pub. Date: Oct. 5, 2017

(65) Prior Publication Data
US 2019/0339186 A1  Nov. 7, 2019

Related U.S. Application Data

(60) Provisional application No. 62/317,102, filed on Apr. 1, 2016.

(51) Int. Cl.
*G01N 15/14* (2006.01)
*G01N 15/06* (2006.01)
(Continued)

(52) U.S. Cl.
CPC ........... *G01N 15/065* (2013.01); *G01N 15/14* (2013.01); *G01N 2015/1062* (2013.01);
(Continued)

(58) Field of Classification Search
CPC ....... G01N 2015/1486; G01N 15/1459; G01N 2021/6439; G01N 21/6428;
(Continued)

(56) References Cited

U.S. PATENT DOCUMENTS 5,903,338 A * 5/1999 Mavliev ............... G01N 15/065
356/338
6,491,872 B1 * 12/2002 Wick ................... G01N 1/2273
422/548
(Continued)

FOREIGN PATENT DOCUMENTS

JP          6522864      5/2019
JP        2019516085     6/2019
(Continued)

OTHER PUBLICATIONS

"International Application Serial No. PCT/US2017/025403, International Preliminary Report Patentability dated Apr. 24, 2018", 7 pgs.
(Continued)

*Primary Examiner* — Michael P Stafira
(74) *Attorney, Agent, or Firm* — Schwegman Lundberg & Woessner, P.A.

(57) ABSTRACT

Various embodiments include methods and apparatuses to reduce false-particle counts in a water-based condensation particle counter (CPC). In one embodiment, a cleanroom CPC has three parallel growth tube assemblies. A detector is coupled to an outlet of each of the three parallel growth tube assemblies, and is used to compare the particle concentrations measured from each of the three growth tube assemblies. An algorithm compares the counts from the three detectors and determines when the particles counted are real and when they are false counts. Any real particle event shows up in all three detectors, while false counts will only be detected by one detector. Statistics are used to determine (Continued)

at which particle count levels the measured counts are considered to be real versus false. Other methods and apparatuses are disclosed.

24 Claims, 7 Drawing Sheets

(51) Int. Cl.
*G01N 35/00* (2006.01)
*G01N 15/10* (2006.01)

(52) U.S. Cl.
CPC .............. *G01N 2015/1486* (2013.01); *G01N 2015/1488* (2013.01); *G01N 2035/00653* (2013.01)

(58) Field of Classification Search
CPC ....... G01N 15/1434; G01N 2015/0693; G01N 2015/1006; G01N 33/5091; G01N 15/06; G01N 21/53; G01N 21/9501; G01N 33/49; G01N 15/0618; G01N 15/147; G01N 33/5094; G01N 15/065; G01N 15/1429; G01N 15/1463; G01N 2015/0065; G01N 33/80; G01N 15/0205; G01N 15/1404; G01N 15/1468; G01N 15/1475; G01N 1/30; G01N 2015/0038; G01N 2015/0046; G01N 2015/0053; G01N 2015/008; G01N 2015/1037; G01N 2015/1411; G01N 2015/1413; G01N 2015/1452; G01N 2015/1488; G01N 2021/058; G01N 21/94; G01N 21/956; G01N 2201/06113; G01N 2223/413; G01N 33/4915; G01N 15/00; G01N 15/02; G01N 15/1031; G01N 15/12; G01N 15/1245; G01N 15/14; G01N 15/1436; G01N 1/38; G01N 2015/1062; G01N 2015/1477; G01N 2021/4707; G01N 2021/4769; G01N 2021/6417; G01N 2021/6441; G01N 2035/0491; G01N 21/47; G01N 21/6458; G01N 21/6486; G01N 21/65; G01N 21/8806; G01N 21/8851; G01N 2223/419; G01N 2223/638; G01N 2223/641; G01N 2223/652; G01N 23/046; G01N 23/20; G01N 27/02; G01N 27/403; G01N 2800/32; G01N 33/2888; G01N 33/5005; G01N 33/56972; G01N 33/574; G01N 35/04; G01N 35/1095; G01N 15/0227; G01N 15/0266; G01N 15/0656; G01N 15/1056; G01N 15/1425; G01N 15/1484; G01N 1/02; G01N 1/40; G01N 2001/028; G01N 2015/0011; G01N 2015/0076; G01N 2015/0084; G01N 2015/03; G01N 2015/0681; G01N 2015/1493; G01N 2035/00524; G01N 2035/00534; G01N 2035/00752; G01N 2035/00801; G01N 2035/00891; G01N 2035/0412; G01N 21/4785; G01N 21/78; G01N 2201/062; G01N 2201/064; G01N 2201/1247; G01N 2223/04; G01N 2223/1016; G01N 2223/304; G01N 2333/4712; G01N 2333/765; G01N 23/083; G01N 2800/12; G01N 2800/26; G01N 2800/324; G01N 33/4833; G01N 33/543; G01N 33/54313; G01N 33/54326; G01N 33/6887; G01N 33/6893; G01N 33/746; G01N 33/76; G01N 33/96; G01N 35/00722; G01N 35/0099; G01N 7/10; G01J 1/0214; G01J 1/0219; G01J 1/0266; G01J 1/0425; G01J 1/0437; G01J 1/4228; G01J 1/429; G01J 2001/442; G02B 6/0229; G02B 6/12004

See application file for complete search history.

(56) References Cited

U.S. PATENT DOCUMENTS

| | | |
|---|---|---|
| 2006/0126056 A1 | 6/2006 | Roberts et al. |
| 2008/0137065 A1 | 6/2008 | Oberreit et al. |
| 2010/0263731 A1 | 10/2010 | Hopke et al. |
| 2014/0033915 A1 | 2/2014 | Hering et al. |
| 2015/0160105 A1* | 6/2015 | Caldow ................ G01N 15/065 356/246 |

FOREIGN PATENT DOCUMENTS

| | | |
|---|---|---|
| KR | 101972921 | 4/2019 |
| WO | 0020626 | 4/2000 |
| WO | 0148571 | 7/2001 |
| WO | 2014058882 | 4/2014 |
| WO | 2016180906 | 11/2016 |
| WO | WO-2017173285 A1 | 10/2017 |

OTHER PUBLICATIONS

"International Application Serial No. PCT/US2017/025403, International Search Report dated Aug. 18, 2017", 3 pgs.
"International Application Serial No. PCT/US2017/025403, Written Opinion dated Aug. 18, 2017", 9 pgs.
"European Application Serial No. 17776785.2, Extended European Search Report dated Apr. 16, 2019", 10 pgs.

* cited by examiner

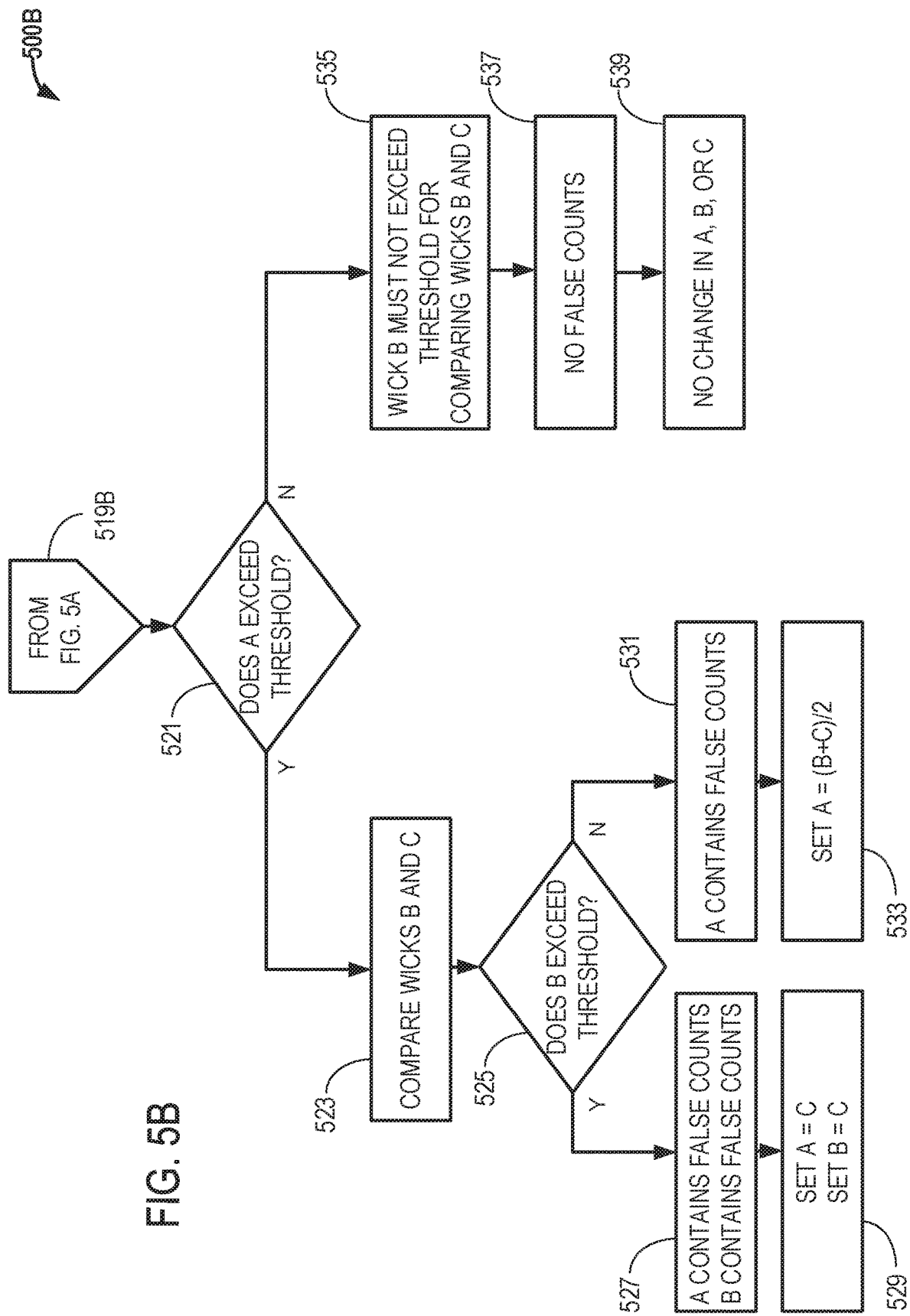

REDUCING FALSE COUNTS IN CONDENSATION PARTICLE COUNTERS

CLAIM OF PRIORITY

This application is a U.S. national stage application filed under 35 U.S.C. & 371 from International Application Serial No. PCT/US2017/025403, filed on Mar. 31, 2017, and published as WO 2017/173285 on Oct. 5, 2017, which claims the benefit of priority to U.S. Provisional Patent Application No. 62/317,102, filed on Apr. 1, 2016, and entitled, "REDUCING FALSE COUNTS IN A CONDENSATION PARTICLE COUNTER," which applications are hereby incorporated by reference in their entireties.

BACKGROUND

Condensation Particle Counters (CPCs) have traditionally had high false-count rates, especially when compared with optical particle counters. In an optical particle counter, false counts are usually caused by optical or electrical noise, and can often be filtered out or eliminated because the false counts have scattering characteristics that create pulses that look different than pulses from real particles. In a CPC however, false counts are caused internal to the CPC when particles are formed within the instrument. Since these particles then grow the same as the particles being measured, the false-count particles look the same as the real particles, thereby making it difficult or impossible to distinguish between real counts and false counts. Consequently, eliminating false counts in a CPC is an exceedingly difficult task.

Moreover, the high false-count rates are typically more prevalent in water-based CPCs as compared with CPCs based on other types of working fluids (e.g., alcohol based CPCs using, for example, isopropanol or butanol). Previous attempts by various manufacturers to develop a high flow rate CPC with a low false-count rate for use in cleanroom applications have been unsuccessful. While some approaches yield very good false-count rates initially, these approaches have been unable to sustain these low false-count rates for significant lengths of time.

Since CPCs have been typically used to measure higher concentrations of particles, this high false-count rate has not been an issue in most applications. However, the high false-count rate is a significant problem for measuring low particle concentrations as found in, for example, cleanrooms and environments in which electronics manufacturing processes occur. The high false-count rate becomes even more critical with the increased sample flow rate of a cleanroom CPC, which is typically 2.83 liter per minute (0.1 ft$^3$ per minute).

However, as volumetric sample flow rates increase, any working fluid that drains in to the flow path has a tendency to create bubbles or other forms of small droplet. The small droplets then grow into large particles that are detected by an optical particle detector within the CPC. Since these counts are generated internally to the CPC and are not caused by actual particles from a monitored environment, the internally-generated counts are considered "false-particle counts" and occur even when the particle counter is sampling clean HEPA-filtered air.

The performance of a CPC is rated by the number of false counts over a specified time period. For example, a semiconductor cleanroom may require less than six false counts per hour. Consequently, in general, the lower the number of false counts, the better the instrument. The disclosed subject matter describes techniques and designs to reduce or eliminate false-particle counts in a CPC.

BRIEF DESCRIPTION OF THE DRAWINGS

FIGS. 5A and 5B show a method using a decision tree-based algorithm to reduce or eliminate false counts in a CPC.

DETAILED DESCRIPTION

Figure 1:
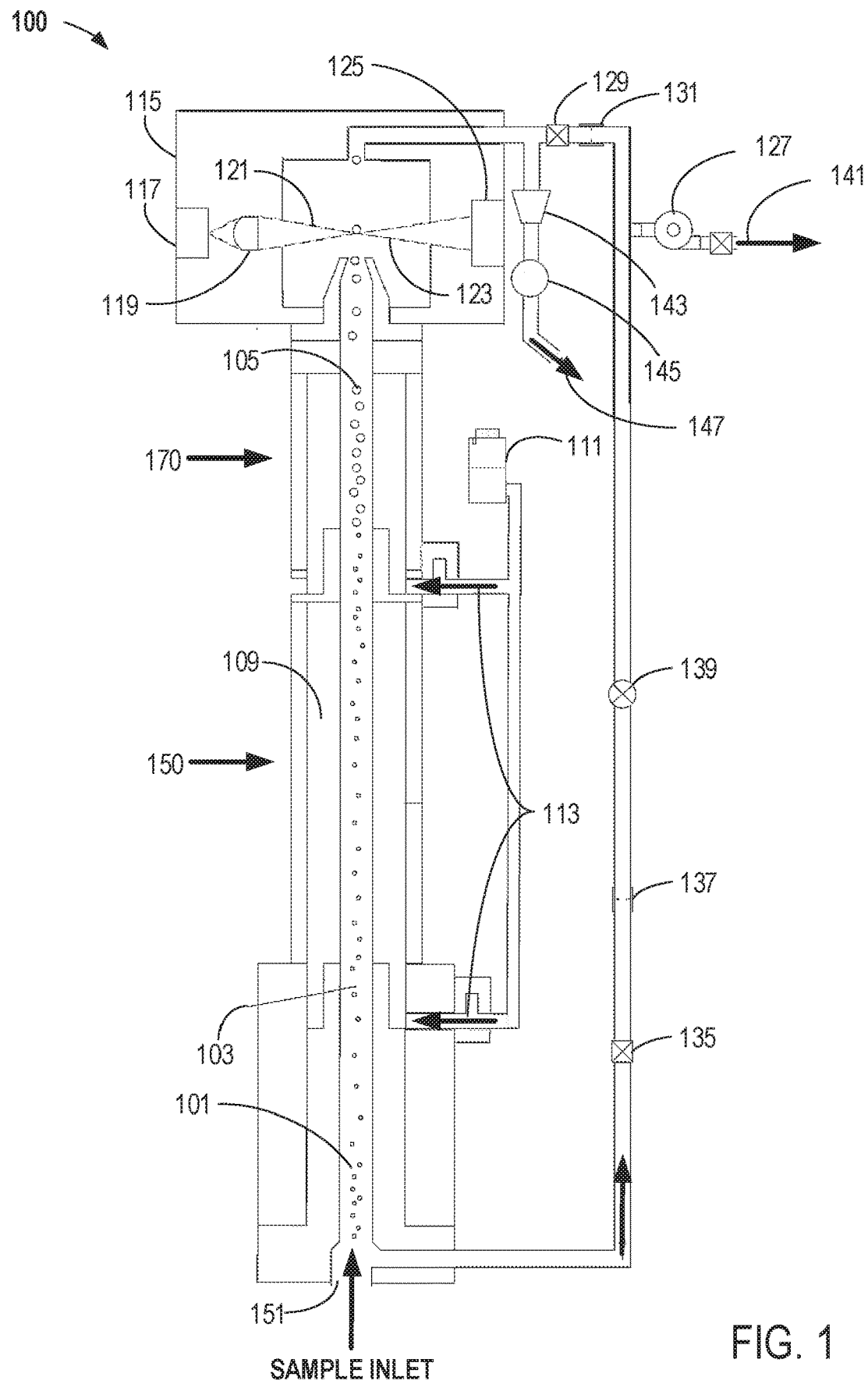
FIG. 1 shows a generalized view of a water-based condensation particle counted (CPC)

Reported count rates in contemporaneous water-based condensation particle counters (CPCs) are generally not acceptable for cleanroom applications due to the high false-particle count rate. Current cleanroom requirements (e.g., in the semiconductor industry) specify a stringent false-count rate of less than six counts per hour. Various embodiments disclosed herein include techniques and designs that were developed specifically to reduce or eliminate false counts caused by various factors, such as water bubbles or empty water droplets (e.g., detected "particles" not containing an actual particle serving as a nucleation point). Typically, these particles are created in "events" that result in a burst of particles, varying from several particles to tens and even hundreds of particles or more. These are short events (lasting for seconds), and are separated by long periods of time with no particles generated, but similar events can happen in the real world. However, since these events occur within the growth tube, statistically, the events will only occur in one growth tube at any given time. If a burst of particles occurs in only one growth tube, it is caused by a false-count event. Any real event would be detected in all three growth tubes.

In one embodiment, the cleanroom CPC disclosed herein uses three growth tubes ("wicks") arranged in parallel with each other in order to increase the sample flow rate of the instrument. In one exemplary embodiment, the disclosed subject matter adds a separate individual particle detector to an outlet of each of the three growth tubes and compares signals measured at the outlets of each of the three individual particle detectors to determine if the events being detected are real counts, caused by actual particles from the monitored environment, or false counts. False counts are caused by events that occur in one growth tube at a time and therefore will only be detected by one of the three particle detectors. As explained in greater detail below, real particles are equally likely to pass through any one of the three growth tubes, and as a result, statistically, all three detectors will sense and count particles. Events that occur on only one detector are false counts and can be eliminated, greatly reducing or eliminating the false-count rate of the CPC.

In general, a condensation particle counter (also known as a condensation nucleus counter) is used to detect particles in a monitored environment that are too small to scatter enough light to be detected by conventional detection techniques (e.g., light scattering of a laser beam in an optical particle counter). The small particles are grown to a larger size by condensation formed on the particle. That is, each particle serves as a nucleation point for the working fluid; a vapor, which is produced by the instrument's working fluid, is condensed onto the particles to make them larger. After achieving growth of the particle due to condensation of the working fluid vapor onto the particle, CPCs function similarly to optical particle counters in that the individual droplets then pass through the focal point (or line) of a laser beam, producing a flash of light in the form of scattered radiation. Each light flash is counted as one particle. The science of condensation particle counters, and the complexity of the instrumentation, lies with the technique to condense vapor onto the particles. When the vapor surrounding the particles reaches a specific degree of supersaturation, the vapor begins to condense on the particles. The magnitude of supersaturation determines the minimum detectable particle size of the CPC. Generally, the supersaturation profile within the instrument is tightly controlled.

While there are several methods which can be used to create condensational growth, the most widely used technique is a continuous, laminar flow method. Continuous flow laminar CPCs have more precise temperature control than other types of CPCs, and they have fewer particle losses than instruments that use turbulent (mixing) flow. In a laminar flow CPC, a sample is drawn continuously through a conditioner region which is saturated with vapor and the sample is brought to thermal equilibrium. Next, the sample is pulled into a region where condensation occurs. In contrast, in an alcohol-based (e.g., isopropanol or butanol) CPC, the conditioner region is at a warm temperature, and the condensation region (saturator) is relatively cooler. Water has very high vapor diffusivity, so a laminar flow water-based CPC with a cool condensation region does not work thermodynamically. In a laminar flow water-based CPC, the conditioner region is cool, and the condensation region is relatively warmer.

Water-based CPCs have a clear set of advantages over alcohol-based CPCs. Water is non-toxic, environmentally friendly, and easy to procure. Water however, also has a few disadvantages. In general, the liquid purity is not as tightly controlled for water as for alcohols purchased from chemical supply houses. The impurities in the water may build up in the "wick" (described below), and eventually cause the wick material to become ineffective. To counteract this impurity effect, distilled or high-purity water is frequently utilized. Additionally, the wicks are often field replaceable by an end-user. In some environments where extremely low particle counts are expected to be present (e.g., a semiconductor-fabrication facility), the end-user may use water specifically prepared and packaged for use in normal-phase liquid chromatography (NPLC). NPLC water is ultra-pure water with a low ultra-violet (UV) absorbance, often filtered through, for example, a 0.2 micrometer (μm) filter, and packaged in solvent-rinsed amber glass bottles and sealed under an inert atmosphere such as nitrogen. The use of NPLC water can help to reduce or eliminate false-particle counts from contaminants (e.g., ions, particles or bacteria) that may ordinarily be present in the water.

In the following detailed description, reference is made to the accompanying drawings that form a part of the false-particle reduction techniques and in which is shown, by way of illustration, specific embodiments. Other embodiments may be utilized and, for example, various thermodynamic, electrical, or physical changes may be made without departing from the scope of the present disclosure. The following detailed description is, therefore, is to be taken in an illustrative sense rather than in a limiting sense.

With reference now to FIG. 1, a generalized view of a water-based condensation particle counter (CPC) 100 is shown. The water-based CPC 100 is used to monitor a particle concentration level within a given environment (e.g., a semiconductor-fabrication facility). The thermodynamic considerations governing operations of water-based CPCs are known in the art and therefore will not be discussed in significant detail herein.

The water-based CPC 100 is shown to include a flow path 101 directing an aerosol sample flow 103 through a porous media 109. The porous media 109 is also referred to as a wick and may comprise one or more various types of hydrophilic material. The porous media 109 that surrounds at least a portion of the flow path may comprise a continuous material from the sample inlet 151 to at or near an optical particle detector 115 (described in more detail below). Alternatively, the porous media 109 may comprise different sections or portions along the flow path 101 of the aerosol sample flow 103 (the aerosol sample flow 103 being shown within the flow path 101).

In this embodiment, the porous media 109 is supplied with liquid water from a water fill bottle 111 along two water-inlet paths 113. Depending on a specific design of the water-based CPC 100, the number of water-inlet paths 113 may decrease to a single inlet path or the number of inlet paths may increase. The actual number of water-inlet paths 113 designed into the water-based CPC 100 may be determined by a person of ordinary skill in the art based on aerosol flow rates, thermodynamics of the system, and other considerations of the water-based CPC 100. The first (closest to the sample inlet 151) of the water-inlet paths 113 supplies water to the porous media 109 just before a cooled conditioner portion 150 of the water-based CPC 100. The second of the water-inlet paths 113, downstream of the first, supplies additional water just before a heated-growth portion 170 of the water-based CPC 100. As noted in FIG. 1, smaller particles from the sample inlet 151 have "grown" in size due to condensation of water vapor onto the particles. Larger particles 105 have a different and generally larger scattering signature than smaller particles. Consequently, larger particles 105 with a condensation layer are more readily detected by the optical particle detector 115 than the smaller particles entering the sample inlet 151.

For example, the larger particles 105 in the flow path 101 comprising the aerosol stream cross a "focus point" of a beam of light 121 emitted by a light source 117, typically a solid-state laser diode. The focus point is formed by an optical element 119 focusing light (e.g., to a diffraction-limited point or line that is generally perpendicular to both the direction of the beam of light 121 output from the light source 117 and the flow path 101). Scattered radiation 123 individually created by each of the larger particles 105 is sensed by an optical sensor 125. The larger particles 105 continue out of the optical particle detector 115 and are either captured by a filter 129 or continue into a water separator 143. Either periodically or continuously, the water separator 143 is drained by a drain pump 145 to a water drain discharge 147.

Overall aerosol flow through the flow path 101 is maintained by a sample-flow pump 127. In the embodiment shown in FIG. 1, the aerosol flow rate is maintained by a critical orifice 131. In other embodiments, a standard orifice or other type of flow control mechanism may be employed. Critical orifices are frequently used in gas-flow sampling instruments as they are able to maintain a constant flow rate provided a sufficient differential pressure is maintained across the orifice. The sample-flow pump 127 may either be a pump internal to the water-based CPC 100 or may be an externally-connected pump. In some embodiments, the water-based CPC 100 may be connected directly to a vacuum-supply source plumbed within a facility (e.g., a vacuum-supply source of the semiconductor-fabrication facility). Pump exhaust 141 is filtered prior to release to ambient air so as not to increase a contamination level of the monitored environment.

The sample-flow pump 127 may also provide a flow from the sample inlet 151 through a secondary gas-flow path that includes a transport flow filter 135, a second critical orifice 137 and an optional transport flow valve 139. The optional transport flow valve 139 may be used to reduce a total gas flow rate if the differential pressure across the second critical orifice 137 is not sufficient to maintain a constant pressure.

Figure 2:
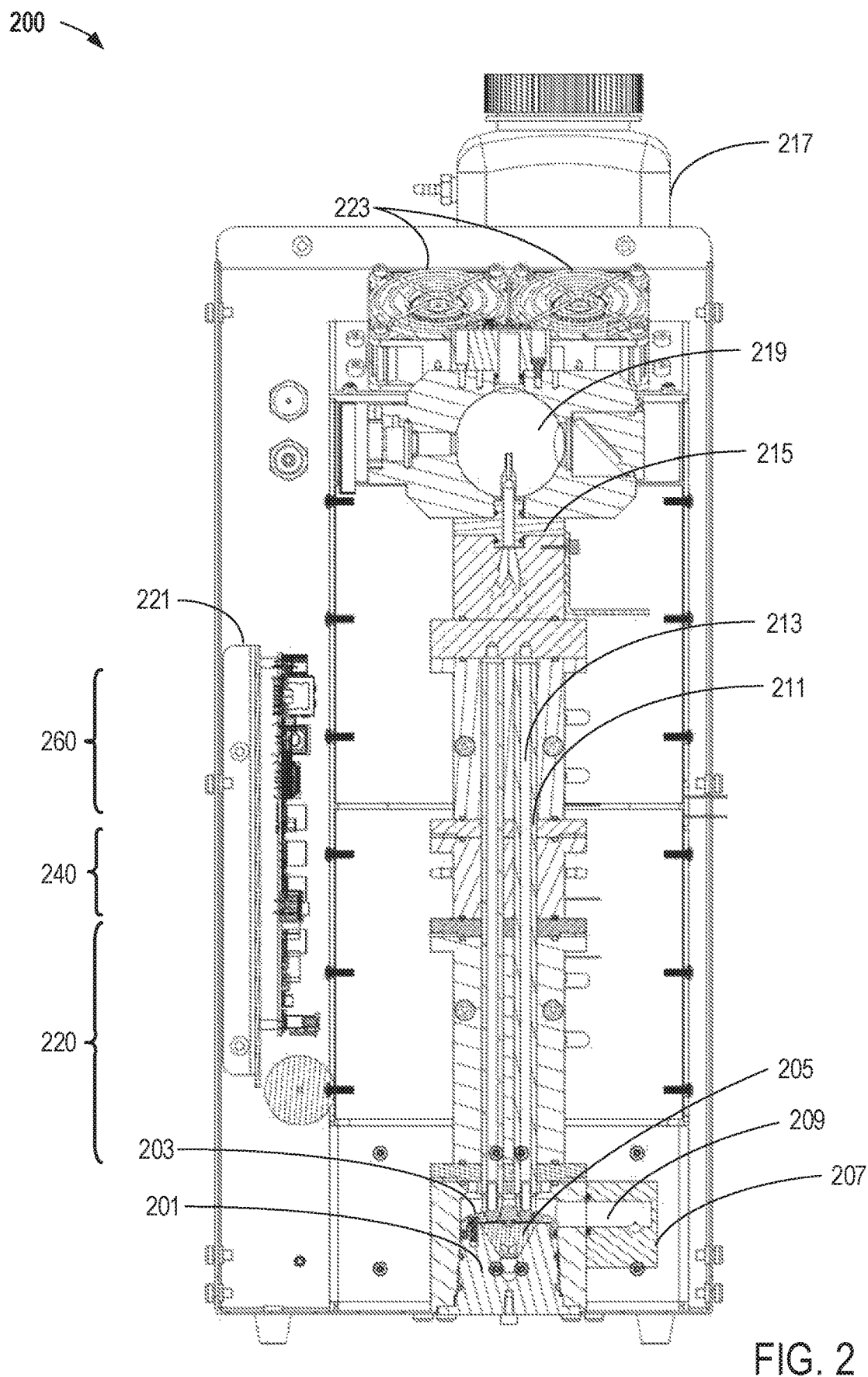
FIG. 2 shows a cross-section of a water-based CPC that incorporates a plurality of wicks that are used to form multiple flow paths (e.g., parallel growth tubes) to form one type of false-particle count reduction embodiment disclosed herein.
Figure 3A:
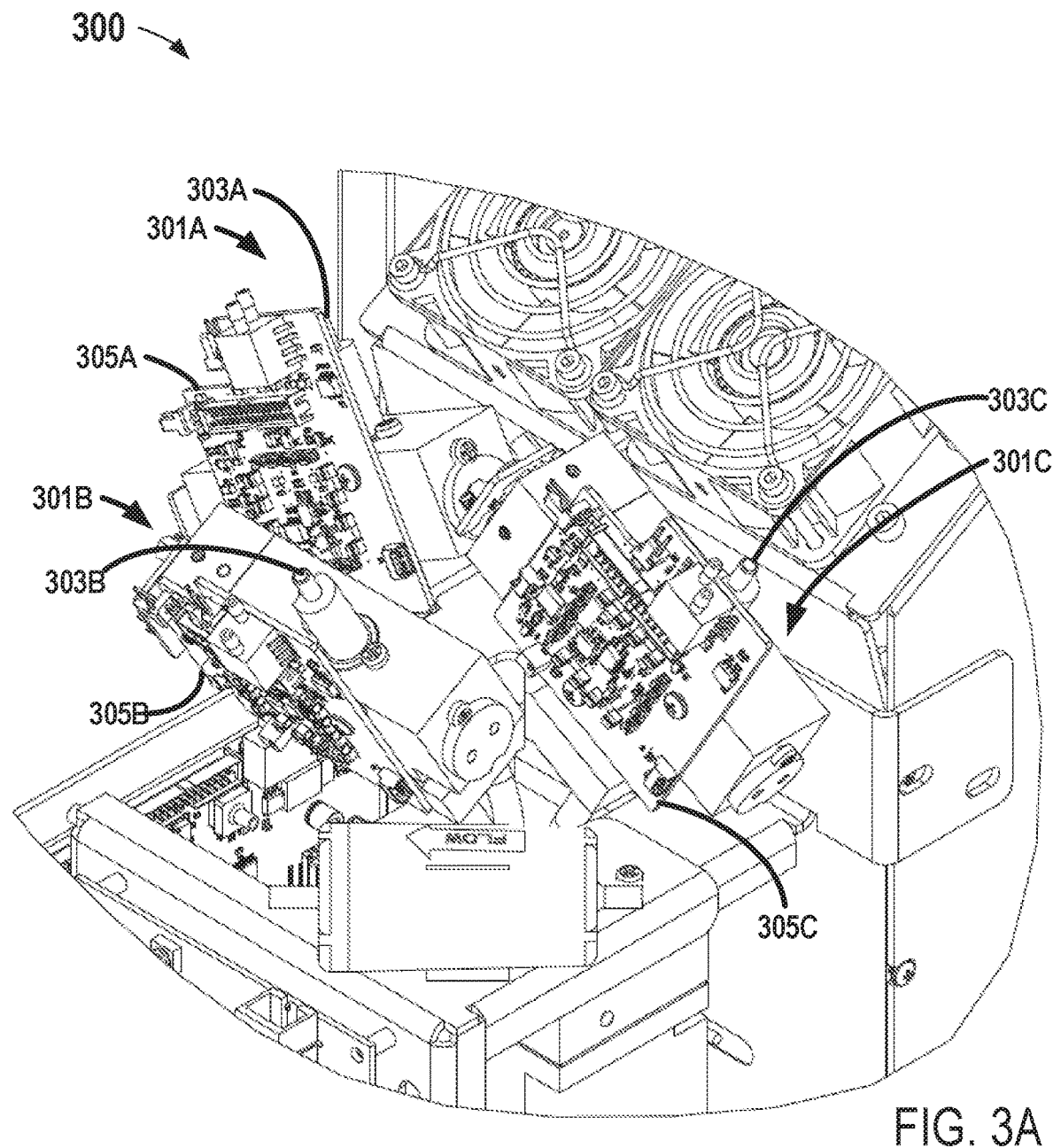
FIG. 3A shows an isometric view of an embodiment of a portion of a water-based CPC having a plurality of multiple flow paths, as in FIG. 2, and also incorporates separate particle detectors coupled to each of the individual flow paths.
Figure 3B:
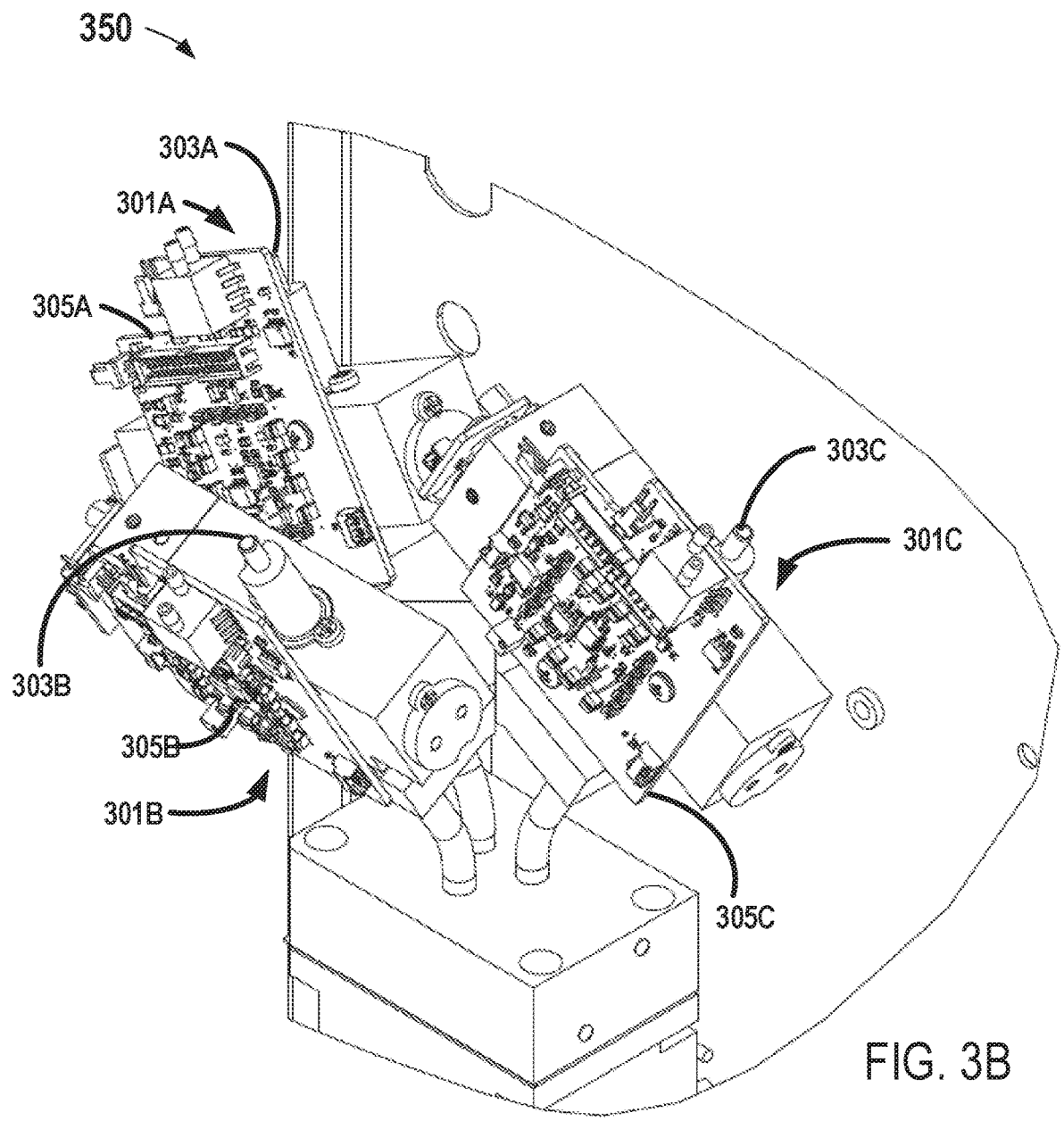
FIG. 3B shows another isometric view of an embodiment of a detector portion of a water-based CPC of FIG. 3A, with certain components removed to more clearly indicate each of the separate optical particle detectors.
Figure 4:
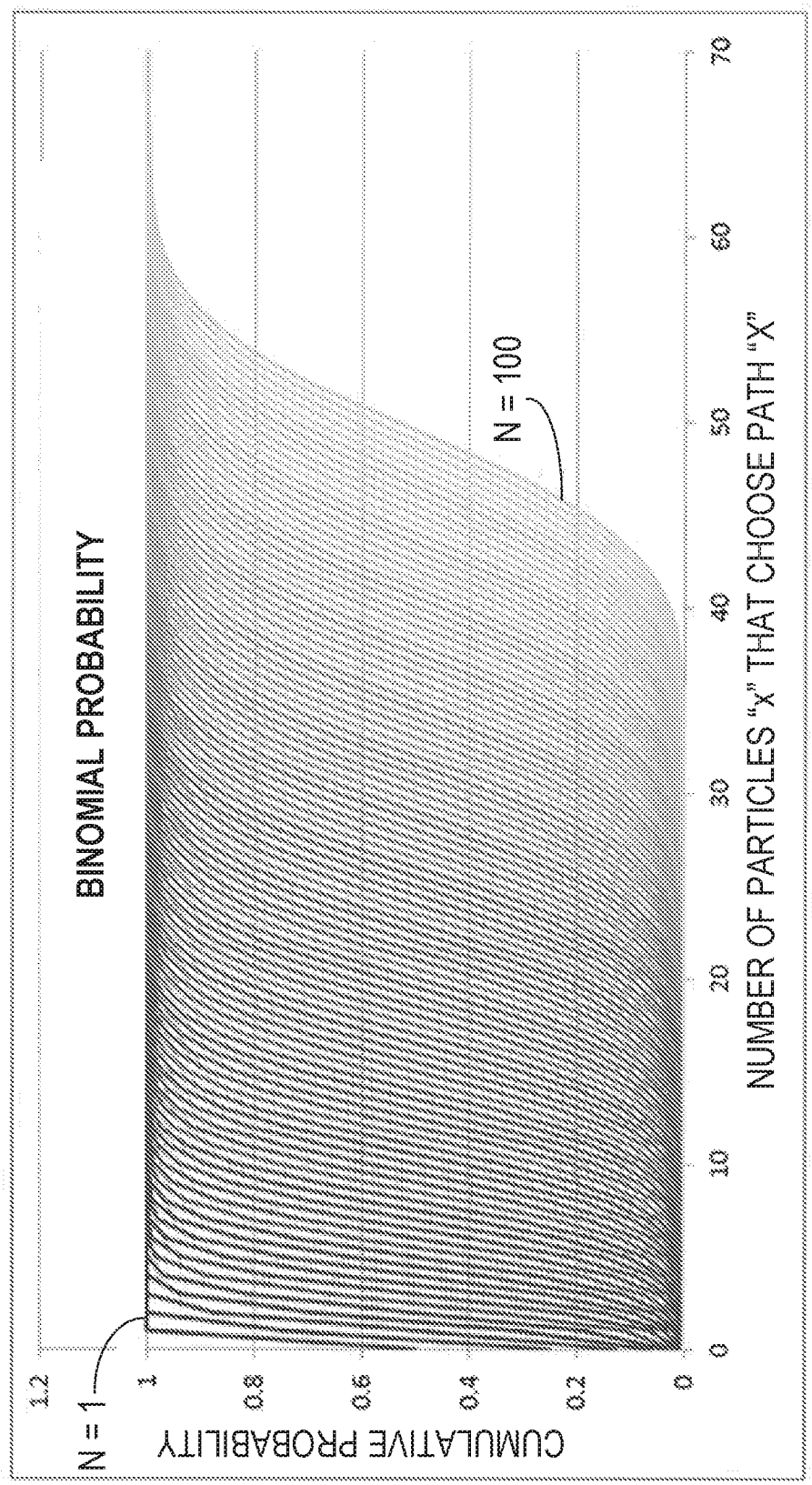
FIG. 4 is a graph showing the cumulative probability that, for n=1 to 100 particles, and given two equally probable paths, the cumulative probability that up to "x" particles choose a given path, "X"

Referring now to FIG. 2, a cross-section of a water-based CPC is shown that incorporates a plurality of wicks that are used to form multiple flow paths (e.g., parallel growth tubes) to form one type of false-particle count reduction embodiment disclosed herein. The water-based CPC 200 functions similarly in basic operation to the water-based CPC 100 of FIG. 1. Additionally, the water-based CPC 200 is shown to include a removable wick cartridge 201 that may be configured to be readily removable by the end-user. The removable wick cartridge 201 includes a wick stand 203 that is affixed over the removable wick cartridge 201 and a conical section 205. Adjacent to the removable wick cartridge 201 is a drain sidecar 207 having a drain reservoir 209 formed therein.

A sample inlet (not shown specifically in FIG. 2 but similar to the sample inlet 151 of FIG. 1) is located near a lower edge of the removable wick cartridge 201. Particles contained within an aerosol stream arriving through the sample inlet traverse one or more flow paths 213 through one or more wicks 211. In an example, three wicks 211 are used to form the flow paths 213. However, the number of wicks 211 may be changed by the manufacturer depending on factors related to maintaining a sufficiently low Reynolds number to maintain a laminar flow of the aerosol stream through the one or more flow paths 213. Such factors are known to a skilled artisan and include determining a ratio of inertial forces to viscous forces of the aerosol flow based on a mean velocity and density of the fluid in the aerosol stream, as well as dynamic and kinematic viscosities of the fluid, and a characteristic linear dimension relating to an internal cross-section of the wicks 211. Additionally, a single wick 211 with multiple paths formed therein (e.g., by "drilling" out or otherwise forming or opening more paths) may also be used.

The wick stand 203 splits the incoming aerosol stream and contains a number of outlet paths equal to the number of wicks. In the embodiment depicted by FIG. 2, the wick stand 203 has three outlet paths. The wick stand also provides a physical mechanical-interface onto which the wicks 211 are mounted. When more than one wick 211 is used, a flow joiner 215 combines particles from the three aerosol streams into a single aerosol stream immediately prior to a particle detection chamber 219. The particle detection chamber 219 may be similar to the optical particle detector 115 of FIG. 1. More detail regarding the wicks and the wick stands may be found with reference to PCT Application US2016/019083, filed 23 Feb. 2016.

One or more cooling fans 223 reduce or eliminate any excess heat produced within the water-based CPC 200 by, for example, one or more circuit boards 221, as well as heating elements and thermo-electric devices.

Similar to the basic thermodynamic principles discussed with reference to the water-based CPC 100 of FIG. 1, the water-based CPC 200 of FIG. 2 shows a conditioner portion 220, an initiator portion 240, and a moderator portion 260. The conditioner portion 220 is cooled to begin the process of forming a condensate on particles in the aerosol stream. The initiator portion 240 is heated and is the portion of the water-based CPC 200 where condensate is formed on each of the individual particles. The moderator portion 260 is cooled sufficiently, relative to the initiator portion 240, such that moist air entering the particle detection chamber 219 is reduced or eliminated. A water fill bottle 217 provides a reservoir of clean water (e.g., NPLC, other ultra-pure water, or distilled water) to keep the wicks 211 hydrated to provide water vapor in the flow paths 213 to condense on the particles. However, either an excess volume of water, or water provided to the wicks 211 too rapidly (e.g., when supplied in "spurts"), can contribute to the formation of either water bubbles or empty droplets not containing any particles. Either of these conditions can lead to an increase in false-particle counts.

In one embodiment, water from the water fill bottle 217 is supplied to the wicks 211 by gravity feed. In another embodiment, water from the water fill bottle 217 is supplied to the wicks 211 periodically through water pumps (not shown). In another embodiment, water from the water fill bottle 217 is supplied to the wicks 211 either continuously or periodically through a syringe-injection arrangement (not shown specifically but understood by a skilled artisan). In another embodiment, the water fill bottle may be either slightly pressurized or driven with a pneumatic or hydraulic ram system to act as a type of syringe-injection system. In another embodiment, water from the water fill bottle 217 is supplied to the wicks 211 periodically from either the water pumps or one of the types of syringe-injection system through a pulsation damper (e.g., a reservoir designed to reduce or eliminate rapid increase in volumetric flow of the water). By supplying the water either continuously (e.g., through syringe-injection) or periodically (e.g., utilizing the pulsation damper mechanism), excess water over a short period of time to the wicks is reduced or eliminated.

In various embodiments, hydrogen peroxide may be added to the water fill bottle 217 to prevent bacterial growth. In various embodiments, silver impregnation of the wicks or other bio-inhibitors, such as UV illumination, may be employed either separately from or in combination with hydrogen peroxide added to the water fill bottle 217. Like particles in the aerosol stream, bacteria formed within the water can be the basis of a nucleation point in the flow paths 213. Condensed water on the bacteria flowing into the particle detection chamber 219 will then be counted as a particle. The bacteria therefore can also increase the false-particle count of the CPC.

Generally, regardless of the water delivery technique chosen, air bubbles in delivery lines to the wicks 211 should be avoided to reduce or eliminate water bubbles being formed within the flow paths 213. Also, any dead air volumes within the water delivery paths are avoided.

However, regardless of how the water is supplied to the wicks 211, any excess water should be drained off before it causes bubbles or empty water droplets in the aerosol stream flowing through the flow paths 213. The drain sidecar 207 may include an exhaust-air port, a water-sensor port, and a water-drain port (not shown but readily understood by a person of ordinary skill in the art). The exhaust-air port allows water from the water reservoir to drain more readily by drawing air and may be coupled to, for example, the sample-flow pump 127 (FIG. 1) or another pump mounted either internal to or external to the water-based CPC 200.

When water is supplied to the wicks 211, excess water from the wicks 211 drains into the water reservoir. When the water supply to the wicks 211 is sufficient, the water sensor then supplies a signal to stop the water supply. The water sensor may be electrically coupled by an electrical lead to one of the circuit boards 221 to determine when water is present in the drain sidecar 207. A constant air flow through the exhaust-air port of the drain sidecar 207 pulls water from the water reservoir toward the drain sidecar 207. The drain sidecar 207 includes the water sensor that detects when the drain fills with water to a certain predetermined level, at which point the water is extracted by a separate pump.

In other embodiments, the water sensor may instead comprise a temperature sensing device (e.g., a thermocouple or thermistor) or a humidity sensing device to determine when water is present in the drain sidecar 207. After water is detected, the water is pumped out of the drain sidecar 207 through the water-drain port by, for example, a solenoid-activated micro-pump. In a specific exemplary embodiment, the micro-pump may draw water at a variable approximate flow rate of from about 50μ-liters/minute to about 200μ-liters/minute. In other embodiments, the micro-pump may draw water at a substantially constant approximate flow rate of about 150μ-liters/minute. More detail regarding the drain sidecar may be found with reference to PCT Application US2016/019083, filed 23 Feb. 2016.

FIG. 3A shows an isometric view of an embodiment of a detector portion 300 of a water-based CPC having multiple flow paths (e.g., parallel growth tubes), as in FIG. 2, and incorporating separate optical particle detectors 301A, 301B, 301C. Each of the separate optical particle detectors 301A, 301B, 301C is coupled to a respective one of the individual flow paths 213 (see FIG. 2). Consequently, the three separate optical particle detectors 301A, 301B, 301C may be utilized in place of the flow joiner 215 of FIG. 2 that combines particles from the three aerosol streams into a single aerosol stream immediately prior to directing the aerosol stream to the single particle detection chamber 219.

Each of the optical particle detectors 301A, 301B, 301C is shown to include a respective aerosol exhaust path 303A, 303B, 303C, and a respective circuit board 305A, 305B, 305C. Each of the circuit boards 305A, 305B, 305C coupled to a respective one of the optical particle detectors 301A, 301B, 301C may include functions such as a laser driver to drive a light source (e.g., similar to or the same as the light source 117 of FIG. 1), particle detection circuitry (e.g., to receive a signal caused by a detected particle from a particle detector (e.g., similar to or the same as the optical sensor 125 of FIG. 1), as well as a microprocessor to calculate various statistical parameters to reduce or eliminate false-particle counts as discussed in more detail with regard to FIGS. 4, 5A, and 5B, below. In other embodiments, a separate micro-processor (not shown) may be electrically coupled to each of the circuit boards 305A, 305B, 305C to calculate the various statistical parameters in addition to other control functions.

After the aerosol stream traverses the respective optical particle detector and exhaust path, any particles in the aerosol stream may then be either captured by a filter 129 or continue into a water separator 143 as shown in FIG. 1.

FIG. 3B shows another isometric view of an embodiment of a detector portion 350 of a water-based CPC of FIG. 3A, with certain components being removed to more clearly indicate each of the separate optical particle detectors 301A, 301B, 301C. Although FIG. 3A and FIG. 3B each show three particle detectors, a skilled artisan will recognize, upon reading and understanding the disclosure provided herein, that more than three (e.g., four, five, six, or more) particle detectors (one per a respective number of wicks), or fewer (e.g., two) may be utilized to realize the benefits of the false-particle reduction or elimination techniques discussed. Generally, a geometric similarity of the flow paths should be considered in any design layout. However, differences in flow path geometries may accounted for by measurement or inference (e.g., based on differences in an inside diameter or area ratios of the various flow paths), and incorporated into the particle count comparison method, discussed with reference to FIGS. 5A and 5B. Also, any differences in counting efficiencies by each the plurality of particle detectors may be considered and factored in for determining a number of actual particles being detected (e.g., if all three detectors are not 100% efficient for a given particle size, a correction factor may be included when determining an actual particle count or false count).

Referring now to FIG. 4, a graph shows the cumulative probability that, for n=1 to 100 particles, and given two equally probable paths, the cumulative probability that up to "x" particles choose a given path, "X." Therefore, with two equally probable paths, these statistics are based on a binomial probability.

As a result of this statistical modeling, a skilled artisan will recognize that false count spikes that originate inside individual wicks can be distinguished from real counts (e.g., actual particles) that originate outside the wicks using a particle counter for each wick along with statistics. The false counts can be distinguished since it is unlikely that a large spike of particles from outside the wicks will be detected in only one wick (assuming equally performing wicks).

For example, if the total particle count in two wicks is 100, then there is only approximately a 5% chance that there are 60 particles in the first wick and 40 in the second wick. A count split between the two wicks of 70 in one wick in 30 in the other is statistically much less likely. Consequently, the binomial statistics, discussed in greater detail below with reference to FIGS. 5A and 5B, serve to calculate the confidence that spikes in a particular wick above a given pre-determined threshold number of particles can be excluded as false counts.

In one test case, a high false-count rate of approximately 42 counts per minute in a three-wick cleanroom-type prototype CPC was measured. However, many of these counts were from air bubbles or empty droplets that originated within one or more of the wicks or along one or more of the individual wick paths. Consequently, most of the counts were not based on actual particles (e.g., particle events within an aerosol stream sampled from within the cleanroom). By applying the algorithms and techniques discussed herein (and discussed in greater detail below), researchers noted a nearly 20-times reduction in false-count rates with a concomitant drop in measured large spikes of particles. Utilizing the techniques and systems disclosed herein resulted in a "filtered" count rate (e.g., after applying the techniques) of 4.7 counts per minute. The filtered count rate only requires data from a "current" time period (e.g., a pre-determined sampling period).

In another use of the techniques, a short time interval "look-back" component can account for sub-threshold false counts that follow an above-threshold spike. Using the look-back component resulted in a count rate of 2.6 counts per minute compared with the raw count rate of 42 counts per minute.

Figure 5A:
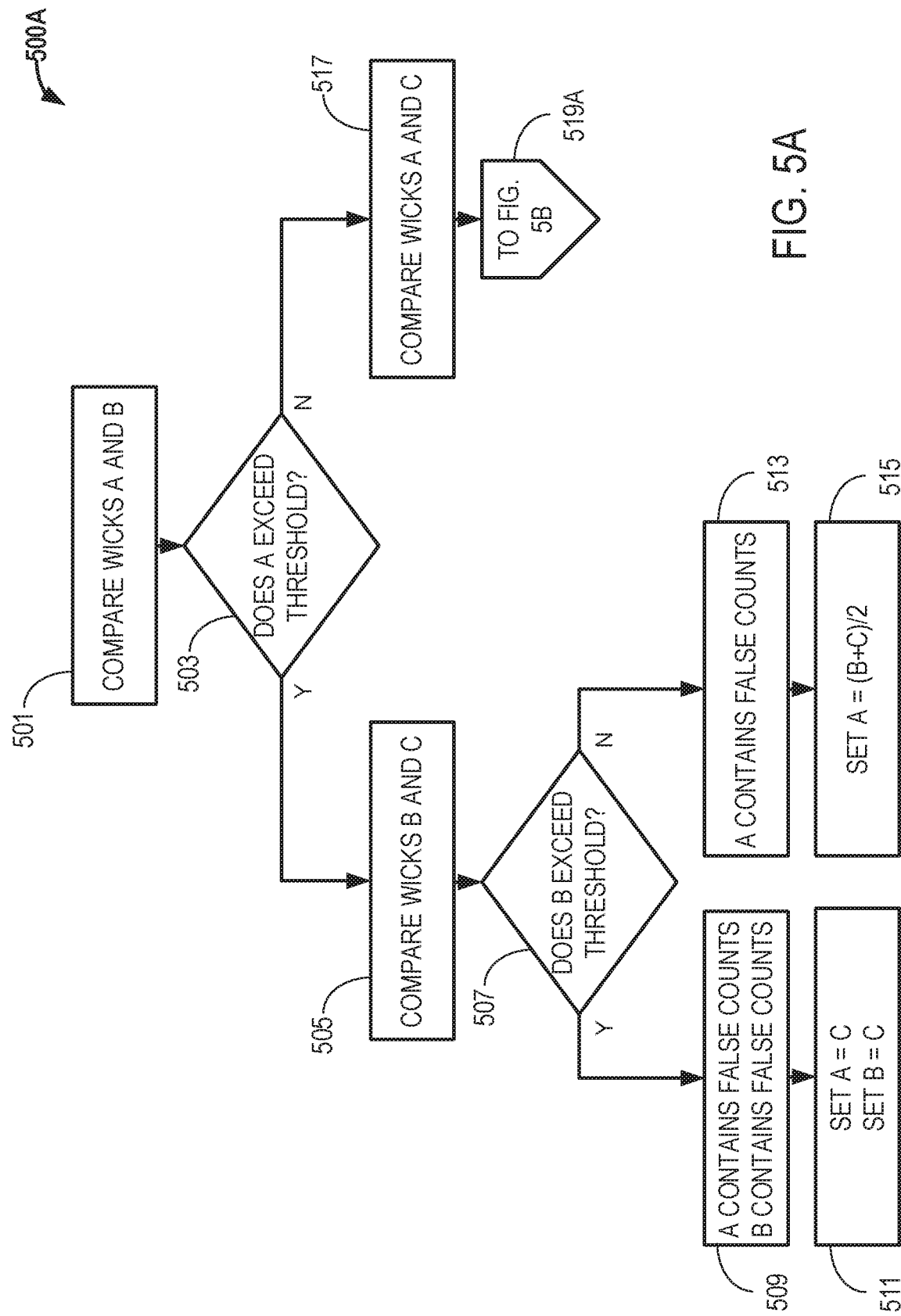

With reference now to FIGS. 5A and 5B, a first portion of the method 500A and a second portion of the method 500B using a decision tree-based algorithm to reduce or eliminate false counts is shown. In general, the decision process as to whether to adjust particle counts proceeds in three steps: (1) order particle counts during a given time interval in the three wicks, A, B, and C, such that the counts in the wicks are arranged so that count A is greater than B, which is greater than C; (2) for each wick pair (i.e., A and B, B and C, and A and C), count the total number of particles in each of the two wicks and, based on the binomial probability discussed above, determine a threshold spike size that would be expected to be improbable for a desired confidence level (e.g., 95%, 99%, 99.9% confidence intervals); and (3) use a decision tree-based algorithm to eliminate probable false counts. The method shown in FIGS. 5A and 5B is thus based on an assumed difference in particle counts in the three wicks and thus is not used in a case where counts the three wicks are all equal.

With reference now to FIG. 5A, the first portion of the method 500A begins at operation 501 by comparing the counts as measured within wicks A and B (ordered by count as noted above). A determination is then made at operation 503 as to whether the count in wick A exceeds the pre-determined threshold value, as noted above. Based on a determination that the threshold value is exceeded, then the counts in wicks B and C are compared at operation 505. A determination is then made at operation 507 as to whether the count in wick B exceeds the pre-determined threshold value.

Based on a determination that the threshold value is exceeded, then at operation 509 the algorithm indicates that wick A and wick B each contain false counts. Accordingly, at operation 511, the count for each of wicks A and B are set to be equal to the count as measured within wick C.

If, however, based on a determination at operation 507 that the count within wick B does not exceed the threshold value, then at operation 513 the algorithm indicates that only wick A, and not wick B, contains false counts. Accordingly, at operation 515, the count from wick A is set substantially or exactly to be equal to the summation of wicks B and C divided by 2 (i.e., the average count value of wicks B and C).

Referring back again to operation 503, based on a determination that the count within wick A does not exceed the threshold value, then at operation 517, the counts measured within wicks A and C are compared. At operation 519A, the first portion of the method 500A continues from FIG. 5A to FIG. 5B.

Continuing with the second portion of the method 500B, and coming into FIG. 5B from operation 519A (FIG. 5A) at operation 519B, a determination is then made at operation 521 as to whether the count in wick A exceeds the pre-determined threshold value based on the comparison with the count measured within wicks A and C from operation 517 (FIG. 5A).

Based on a determination that the count within wick A exceeds the threshold value, then the counts in wicks B and C are compared at operation 523. A determination is then made at operation 525 as to whether the count in wick B exceeds the pre-determined threshold value.

Based on a determination that the threshold value is exceeded, then at operation 527 the algorithm indicates that wick A and wick B each contain false counts. Accordingly, at operation 529, the count for each of wicks A and B are set to be equal to the count as measured within wick C.

If, however, based on a determination at operation 525 that the count within wick B does not exceed the threshold value, then at operation 531 the algorithm indicates that only wick A, and not wick B, contains false counts. Accordingly, at operation 533, the count from wick A is set to be substantially or exactly equal to the summation of wicks B and C divided by 2 (i.e., the average value of wicks B and C).

Referring back again to operation 521, based on a determination that the count within wick A does not exceed the threshold value, then at operation 535 the algorithm indicates, to get to this point in the second portion of the method 500B, that the count within wick B must not have exceeded the threshold for comparing wicks B and C. Accordingly, there are no false counts in any of the wicks, as indicated by operation 537, and that there is no change needed in the measured counts in wicks A, B, or C as indicated in operation 539.

The decision tree-based algorithm is illustrated in method 500A, 500B of FIGS. 5A and 5B for three wicks. However, a skilled artisan, based on reading and understanding the disclosure provided herein, will recognize that the algorithm can be used for a greater number of wicks (e.g., four, five, six, or more) or a fewer number of wicks (i.e., two). Therefore, the method 500A, 500B can be readily modified for a number of wicks other than three. For example, the skilled artisan may modify the binomial probability used for method 500A, 500B with a trinomial or higher order probability scheme.

The description above includes illustrative examples, devices, and apparatuses that embody the disclosed subject matter. In the description, for purposes of explanation, numerous specific details were set forth in order to provide an understanding of various embodiments of the inventive subject matter. It will be evident, however, to those of ordinary skill in the art that various embodiments of the inventive subject matter may be practiced without these specific details. Further, well-known structures, materials, and techniques have not been shown in detail, so as not to obscure the various illustrated embodiments.

As used herein, the term "or" may be construed in an inclusive or exclusive sense. Additionally, although various exemplary embodiments discussed below focus on particular ways to reduce false-particle counts by eliminating empty water droplets or bubbles being counted as actual particles, other embodiments consider electronic filtering techniques. However, none of these techniques needs to be applied to reducing or eliminating particle counts as a single technique. Upon reading and understanding the disclosure provided herein, a person of ordinary skill in the art will readily understand that various combinations of the techniques and examples may all be applied serially or in various combinations. As an introduction to the subject, a few embodiments will be described briefly and generally in the following paragraphs, and then a more detailed description, with reference to the figures, will ensue.

Although various embodiments are discussed separately, these separate embodiments are not intended to be considered as independent techniques or designs. As indicated above, each of the various portions may be inter-related and each may be used separately or in combination with other false-count particle reduction techniques discussed herein.

Moreover, although specific values, ranges of values, and techniques are given for various parameters discussed above, these values and techniques are provided merely to aid the person of ordinary skill in the art in understanding certain characteristics of the designs and techniques disclosed herein. Those of ordinary skill in the art will realize, upon reading and understanding the disclosure provided, that these values and techniques are presented as examples only and numerous other values, ranges of values, and techniques may be employed while still benefiting from the novel designs discussed that may be employed to lower false counts in water-based CPCs. Therefore, the various illustrations of the apparatus are intended to provide a general understanding of the structure and design of various embodiments and are not intended to provide a complete description of all the elements and features of the apparatus that might make use of the structures, features, and designs described herein.

Many modifications and variations can be made, as will be apparent to a person of ordinary skill in the art upon reading and understanding the disclosure provided herein. Functionally equivalent methods and devices within the scope of the disclosure, in addition to those enumerated herein, will be apparent to a person of ordinary skill in the art from the foregoing descriptions. Portions and features of some embodiments may be included in, or substituted for, those of others. Many other embodiments will be apparent to those of ordinary skill in the art upon reading and understanding the description provided. Such modifications and variations are intended to fall within a scope of the appended claims. Therefore, the present disclosure is to be limited only by the terms of the appended claims, along with the full scope of equivalents to which such claims are entitled. It is also to be understood that the terminology used herein is for the purpose of describing particular embodiments only and is not intended to be limiting.

The Abstract of the Disclosure is provided to allow the reader to quickly ascertain the nature of the technical disclosure. The abstract is submitted with the understanding that it will not be used to interpret or limit the claims. In addition, in the foregoing Detailed Description, it may be seen that various features may be grouped together in a single embodiment for the purpose of streamlining the disclosure. This method of disclosure is not to be interpreted as limiting the claims. Thus, the following claims are hereby incorporated into the Detailed Description, with each claim standing on its own as a separate embodiment.

What is claimed is:

1. A system to reduce false-particle counts in a condensation particle counter (CPC), the system comprising:
   an aerosol sample inlet configured to be coupled to a sample flow pump;
   an aerosol flow path in fluid communication with and disposed between the aerosol sample inlet and the sample flow pump;
   a plurality of wicks comprising at least a portion of the aerosol flow path, the plurality of wicks each comprising a porous media forming at least a portion of the aerosol flow path; and
   an optical particle detector coupled to an outlet of each of the plurality of wicks to measure counts within respective ones of the plurality of wicks; and
   a processor coupled to each optical particle detector to compare a count from each of the plurality of wicks with a count of remaining ones of the plurality of wicks to make a determination whether the count from any of the plurality of wicks is statistically greater than the counts of the remaining ones of the plurality of wicks, the statistically greater count being a false count.

2. The system of claim 1, further comprising, based on the determination that the count is statistically greater for the count of one of the plurality of wicks, the processor further to reduce the false count by a pre-determined amount in calculating a reported value of particle concentration.

3. The system of claim 1, wherein one count being statistically greater than another count is based on binomial probability theory for a pre-determined confidence interval.

4. The system of claim 1, wherein each of the plurality of wicks is field replaceable by an end-user of the CPC.

5. The system of claim 1, wherein each of the plurality of wicks is silver impregnated to reduce or prevent bacterial growth within the plurality of wicks.

6. The system of claim 1, wherein each of the plurality of wicks is treated with a bio-inhibitor to reduce or prevent bacterial growth within the plurality of wicks.

7. The system of claim 1, further comprising a removable wick cartridge having a wick stand onto which to mount the plurality of wicks, the wick stand being configured to split an incoming aerosol stream into a number of outlet paths equal to a number of the plurality of wicks.

8. The system of claim 7, wherein the removable wick cartridge is in fluid communication with a drain sidecar having a drain reservoir, the drain sidecar being configured to drain excess water supplied to the plurality of wicks to reduce or eliminate bubbles or empty water droplets from flowing in the aerosol flow path.

9. The system of claim 1, wherein a number of the plurality of wicks is based on factors related to maintain a sufficiently low Reynolds number to maintain a laminar flow of an aerosol stream within each of the plurality of wicks.

10. The system of claim 1, wherein a number of the plurality of wicks is three.

11. A system to reduce false-particle counts in a condensation particle counter (CPC), the system comprising:

at least one wick having a plurality of aerosol flow paths formed therein, the at least one wick comprising a porous media; and an optical particle detector coupled to an outlet of each of the plurality of aerosol flow paths to measure counts from respective ones of the plurality of aerosol flow paths; and a processor coupled to each optical particle detector to compare a count from each of the plurality of aerosol flow paths with a count of remaining ones of the plurality of aerosol flow paths to make a determination whether the count from any of the plurality of aerosol flow paths is statistically greater than the counts of the remaining ones of the plurality of aerosol flow paths, the statistically greater count being a false count.

12. The system of claim 11, further comprising, based on the determination that the count is statistically greater for the count of one of the plurality of aerosol flow paths, the processor further to reduce the false count by a pre-determined amount in calculating a reported value of particle concentration.

13. The system of claim 11, wherein one count being statistically greater than another count is based on binomial probability theory for a pre-determined confidence interval.

14. The system of claim 11, further comprising the at least one wick being in fluid communication with a drain sidecar having a drain reservoir, the drain sidecar being configured to drain excess water supplied to the at least one wick.

15. The system of claim 14, further comprising a sensor to provide a signal to stop a water supply when the water supply to the at least one wick is sufficient based on a determination that water is in the drain sidecar.

16. The system of claim 15, wherein the sensor comprises at least one type of sensor selected from sensor types including a water sensor, a temperature sensor, and a humidity sensor.

17. A method of reducing false-particle counts in a condensation particle counter (CPC), the method comprising:
   measuring counts with a particle detector coupled to an outlet of each a plurality of aerosol flow paths within one or more wicks within the CPC;
   making a determination whether a count from any of the plurality of aerosol flow paths is statistically greater than respective counts of remaining ones of the plurality of aerosol flow paths, based on binomial probability theory, the statistically greater count being a false count; and
   reducing the false count by a pre-determined amount in calculating a reported value of particle concentration.

18. The method of claim 17, further comprising draining excess water supplied to the one or more wicks to reduce or eliminate bubbles or empty water droplets from flowing in the plurality of aerosol flow paths within the one or more wicks.

19. The method of claim 17, further comprising flowing a constant supply of air through an exhaust port of a drain coupled to the one or more wicks to reduce or eliminate bubbles or empty water droplets from flowing in the plurality of aerosol flow paths.

20. The method of claim 17, further comprising:
   comparing a count between pairs of the plurality of aerosol flow paths; and
   ordering particle counts from the comparison according to a total number of counts from each of the plurality of aerosol flow paths during a pre-determined time interval.

21. The method of claim 17, further comprising applying a comparison factor to the measured counts for each of the plurality of aerosol flow paths based on differences in geometries of the aerosol flow paths.

22. The method of claim 17, further comprising applying an efficiency factor for each of the particle detectors to account for differences in counting efficiency between the particle detectors.

23. A method of reducing false-particle counts in a condensation particle counter (CPC), the method comprising:
   comparing a count from each of a plurality of wicks from the CPC with a count of remaining ones of the plurality of wicks;
   based on the comparison, making a determination whether the count from any of the plurality of wicks is statistically greater than the counts of the remaining ones of the plurality of wicks, the statistically greater count being a false count; and
   based on the determination that the count is statistically greater for the count of one of the plurality of wicks, reducing the false count by a pre-determined amount in calculating a reported value of particle concentration.

24. The method of claim 23, wherein one count being statistically greater than another count is based on binomial probability theory for a pre-determined confidence interval.

* * * * *